United States Patent [19]
Pal et al.

[11] Patent Number: 6,063,963
[45] Date of Patent: May 16, 2000

[54] AMINO ACID-DERIVED DIAMINOPROPANOLS

[75] Inventors: Biman Pal, Waltham; Siya Ram, Winchester, both of Mass.; Bing Cai, Westfield, N.J.; Yesh P. Sachdeva, Concord, Mass.; Jaechul Shim, Lexington, Mass.; Salah A. Zahr, Acton, Mass.; Emile Al-Farhan, Dedham, Mass.; Richard Gabriel, Swampscott, Mass.

[73] Assignee: Pharm-Eco Laboratories, Inc., Lexington, Mass.

[21] Appl. No.: 08/765,283

[22] PCT Filed: Jul. 5, 1995

[86] PCT No.: PCT/US95/08411

§ 371 Date: Jun. 30, 1997

§ 102(e) Date: Jun. 30, 1997

[87] PCT Pub. No.: WO96/01788

PCT Pub. Date: Jan. 25, 1996

[51] Int. Cl.$^7$ .................................................. C07C 209/36
[52] U.S. Cl. ...................... 564/336; 252/182.12; 560/27; 560/29
[58] Field of Search .............................. 564/336; 560/27, 560/29; 252/182.12

[56] References Cited

U.S. PATENT DOCUMENTS

| | | | |
|---|---|---|---|
| H725 | 1/1990 | Gordon | 548/533 |
| 3,197,510 | 7/1965 | Cyba | 260/584 |
| 4,123,462 | 10/1978 | Best | 260/585 |
| 4,604,402 | 8/1986 | Godfrey, Jr. et al. | 514/333 |
| 4,692,455 | 9/1987 | Gordon | 514/332 |
| 4,740,508 | 4/1988 | Weller, III et al. | 514/255 |
| 4,749,792 | 6/1988 | Natarajan et al. | 546/312 |
| 5,278,148 | 1/1994 | Branca et al. | 514/19 |
| 5,616,726 | 4/1997 | Mitsuda et al. | 548/475 |

FOREIGN PATENT DOCUMENTS

| | | |
|---|---|---|
| 0 389 898A2 | 3/1990 | European Pat. Off. . |
| 0 449 191A1 | 2/1991 | European Pat. Off. . |
| 0 657 415A1 | 6/1995 | European Pat. Off. . |
| 2 200 115 | 7/1988 | United Kingdom . |
| 92/08699 | 5/1992 | WIPO . |
| 93/23368 | 11/1993 | WIPO . |
| 95/01323 | 1/1995 | WIPO . |

OTHER PUBLICATIONS

D. Tourwe, et al., "A New Method for the Solid Phase Synthesis of Hydroxyethylamine Peptide Bond Isosteres: Synthesis of an HIV–1 Protease Inhibitor and of a β–Casomorphin–5 Analogue," *Tetrahedron Letters* 34(34) pp. 5499–5502 (1993).

D. C. Baker, and S. R. Putt, "C–Acylation of Nitromethane. A Synthetic Route to α–Nitroketones," *Synthesis; Communications*, 478–479 (Jun. 1978).

D. Brillion And G. Suavé, "Silica Gel–Catalyzed Knoevenagel Condensation of Peptidyl Cyanomethyl Ketones with Aromatic Aldehydes and Ketons. A Novel Michael Acceptor Functionality for C–Modified Peptides: The Benzylidene and Alkylidene Cyanomethyl Ketone Function", *J. Org. Chem* 57: 1838–1842 (1992).

H. Sasai, et al., "Diasteroselectie Catalytic Asymmetric Nitroaldol Reaction Utilising Rare Earth Li–(R)–BINOL Complex. A Highly Efficient Synthesis of Norstatine", *Tetrahedron Letters*, 35(33): 6123–6126 (1994).

C. L. Lane, "Sodium Cyanoborohydride: A Highly Selective Reducing Agent," Selections from the Aldrichimica Acta (Aldrich–Boranes, Inc.) pp. 67.–74 (1994).

T. Imai, et al., "Organoboron Compounds in Organic Synthesis. 2. Asymmetric Reduction–of–Diakyl Ketones with (R,R)–or (S,S)–2,5–Dimethylborolane," *J. Am. Chem. Soc.*, 108:7402–7404 (1986).

E. J. Corey, et al., "A Stable and Easily Prepared Catlyst for the Enantioselective Reduction of Ketone. Applications to Multistep Syntheses," *J. Am. Chem. Soc.*, 109:7925–7926 (1987).

H. C. Brown, et al., "Chiral Synthesis via Organoboranes. 15. Selectie Reductions. 42. Asymmetric Reduction of Representative Prochiral Ketones with Potassium 9–0–(1,2:5, 6–Di–O–isopropylidine–α–D–glucofuranosyl)–9– boratabicyclo[3.3.1]–nonane," *J. Org. Chem.*, 53:1231–1238 (1988).

A. G. M. Barrett, et al., "Transfer Hydrogenation: A Sterospecific Method for the Conversion of Nitro Alkanes into Amines," *Tetrahedron Letters*, 29(45):5733–5734 (1988).

A. Dondoni, et al., "Iterative, Stereoselective Homologation of Chiral Polyalkoxy Aldehydes Employing 2–(Trimethylsilyl)thiazole as a Formyl Anion Equivalent. The Thiazole Route to Higher Carbohydrates," *J. Org. Chem.*, 54:693–702 (1989).

M. M. Midland, et al., "Asymmetric Reductions of Prochiral Ketones with Lithium [2–[(Benzyloxy)ethyl]–6,6–dimethylbicyclo[3.3.1]–3–nonyl]–9– boratabicyclo[3.3.1] nonane (Lithium NB–Enantride) and its Derivatives," *J. Org. Chem.*, 56:1068–1074 (1991).

D.A. Evans, et al., "Synthetic Applications of Tremethylsilyl Cyanide. An Efficient Synthesis of β–Aminomethyl Alcohols," *J. Org. Chem.*, 39(7):914–917 (1974).

S. Ram and R. E. Ehrenkaufer, "A Facile Synthesis of α–Amino Esters Via Reduction of α–Nitro Esters Using Ammonium Formate as a Catalytic Hydrogen Transfer Agent," *Synthesis; Communications*, 133–135 (Feb. 1986).

*Primary Examiner*—Brian M. Burn
*Attorney, Agent, or Firm*—Hamilton, Brook, Smith & Reynolds, P.C.

[57] ABSTRACT

The present invention relates to a method of forming a 1,3-diamino-3-substituted-2-propanol chemical intermediate from which various chemicals, such as selected protease-inhibitors and other drugs, as well as polymers, can be synthesized.

The method includes contacting a nitromethyl amino acid compound with at least one reducing agent to form the 1,3-diamino-3-substituted-2-propanol chemical intermediate.

24 Claims, No Drawings

AMINO ACID-DERIVED DIAMINOPROPANOLS

BACKGROUND OF THE INVENTION

The inhibition of various proteases has application in treating many medical conditions, such as Alzheimer's disease, retroviral infections, hypotension and hypertension. Many protease-inhibitor compounds have been identified. However, the methods for synthesizing these protease-inhibitor compounds are often complex and/or expensive. Consequently, methods are needed to produce protease-inhibitor compounds through simpler and/or less expensive processes.

SUMMARY OF THE INVENTION

The present invention relates to a method of forming a 1,3-diamino-3-substituted-2-propanol chemical intermediate represented by the following structural formula (structural formula I):

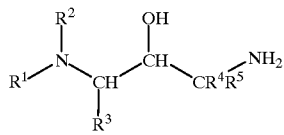

and salts thereof, wherein $R^1$ is a protecting group and $R^2$ is selected from the group consisting of —H, C1–C18 alkyl, aryl, heteroaryl, acetyl and tosyl.

Additionally, $R^3$ is the side-chain of an amino acid wherein the amino acid has the structural formula (structural formula II):

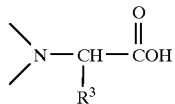

Some examples of suitable amino acids include natural and synthetic α-amino acids, such as alanine, cysteine, 3,5-dibromotyrosine, 3,5-diiodotyrosine, glutamine, glycine, histidine, hydroxylysine, isoleucine, leucine, methionine, phenylalanine, serine, threonine, thyroxine, tryptophane, tyrosine, valine and α-aminobutyric acid. In addition, wherein the amino acid has a chiral center, the side-chain may be from either the D or L isomer of the amino acid. Further, the amino acid may optionally be substituted with one or more substitutents, such as halogen, hydroxyl, sulfonate, C1–C3 alkyl, C1–C3 alkoxy and acyl.

Furthermore, $R^4$ and $R^5$ are each independently selected from the group consisting of —H, alkyl, aryl, nitrile and alkoxycarbonyl. However, it is preferred that $R^4$ and $R^5$ are not both alkoxycarbonyl groups.

This method includes contacting a nitromethyl amino acid compound with at least one reducing agent to form said chemical intermediate. A suitable nitromethyl amino acid compound is represented by the following structural formula (structural formula III):

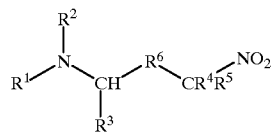

wherein $R^6$ is either

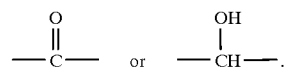

The benefits of this invention include the ability to produce protease-inhibitor compounds, and other drugs, through simpler and/or less expensive synthetic processes.

DETAILED DESCRIPTION OF THE INVENTION

A chemical intermediate, as defined herein, comprises a compound from which various chemicals, such as selected protease-inhibitors and other drugs, as well as polymers, can be synthesized. In a preferred embodiment, the 1,3-diamino-3-substituted-2-propanol chemical intermediate is derived from phenylalanine and comprises a 1,3-diamino-3-benzyl-2-propanol compound.

Suitable protecting groups include protecting groups which generally prevent substitution or addition reactions from occurring with a protected amino group while producing said chemical intermediate according to the method of this invention. Examples of suitable protecting groups include benzyl, t-butyloxycarbonyl (Boc), benzyloxycarbonyl (Cbz), 9-fluorenylmethoxycarbonyl (f-moc), 2,2,2-trichloroethoxycarbonyl, 2-haloethoxycarbonyl, benzoyl, phthalimidyl, diphenylphosphinyl and benzenesulfonyl. Alternatively, $R^1$ and $R^2$ can be combined to form a protecting group, such as dibenzyl.

Alkyl groups of the present invention include straight-chained, branched and cyclic alkyl radicals containing up to about 18 carbons. Suitable alkyl groups may be saturated or unsaturated. Further, an alkyl group may also be substituted one or more times on one or more carbons with substitutents selected form the group consisting of C1–C6 alkyl, C3–C6 heterocycle, aryl, halo, hydroxy, amino, alkoxy and sulfonyl. Additionally, an alkyl group may contain up to 3 heteroatoms. Suitable heteroatoms include nitrogen, oxygen and sulfur.

Aryl groups of the present invention include aryl radicals which may optionally contain up to 3 heteroatoms. An aryl group may also be optionally substituted one or more times with an aryl group or a lower alkyl group. Suitable aryl groups include, for example, phenyl, naphthyl, tolyl, imidazolyl, pyridyl, pyrroyl, thiophenyl, pyrimidyl, thiazolyl and furyl groups.

In one embodiment of the method of this invention, a 1,3-diamino-3-substituted-2-propanol chemical intermediate is formed through two successive reductions of a nitromethyl amino acid compound, having the structure of structural formula III wherein $R^6$ is a carbonyl group (hereinafter a "3-amino-3-substituted-2-oxo-1-nitropropane").

In the first reduction, a 3-amino-3-substituted-2-oxo-1-nitropropane is mixed, in solution, with a carbonyl reducing agent to form a salt of a 1-nitro-3-amino-3-substituted-2-propanol compound, wherein said 1-nitro-3-amino-3-- substituted-2-propanol compound has the following structural formula (structural formula IV):

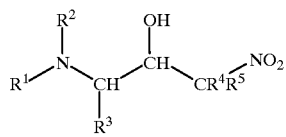

The amount of the carbonyl reducing agent used is an amount which will reduce and hydrogenate at least a portion of the 3-amino-3-substituted-2-oxo-1-nitropropane. Typically, from about 0.1 moles to about 100 moles of a carbonyl reducing agent are used per mole of 3-amino-3-substituted-2-oxo-1-nitropropane.

A carbonyl reducing agent, suitable for the method of this invention, is a chemical or combination of chemicals which will react with a 3-amino-3-substituted-2-oxo-1-nitropropane to reduce and hydrogenate the carbonyl group, but will generally not affect the nitro group. Suitable carbonyl reducing agents include, for instance, sodium borohydride, lithium borohydride, borane, disiamylborane, 9-bora-bicyclo[3.3.1]nonane, lithium tri-tert-butoxyaluminohydride, lithium triethylborohydride and lithium tri(sec-butyl) borohydride.

Suitable solvents for the solution include organic solvents, such as alcohols, esters, ethers and tetrahydrofuran.

It is understood that the 3-amino-3-substituted-2-oxo-1-nitropropane, the carbonyl reducing agent and the solvent may be combined concurrently, sequentially, or in any order or combination. It is also understood that the 3-amino-3-substituted-2-oxo-1-nitropropane may be added as a solid or in solution. It is further understood the carbonyl reducing agent may be added as a solid, liquid, in solution or any combination thereof.

Examples 3 to 6 further describe the reduction of 3-amino-3-benzyl-2-oxo-1-nitropropane compounds to 1-nitro-3-amino-3-benzyl-2-propanol compounds.

The 3-amino-3-substituted-1-nitro-2-propanol can be either in an optically pure form, such as a (2R,3S)-diastereomer or a (2S,3S)-diastereomer, or in a racemic mixture. The 2S diastereomer is preferred. By using chiral reducing agents, the first reduction of 3-amino-3-substituted-2-oxo-1-nitropropane can preferentially produce either the 2S or the 2R diastereomer of 3-amino-3-substituted-1-nitro-2-propanol. Chiral reducing agents suitable for preferentially forming the 2S diastereomer include combinations of a carbonyl reducing agent, such as lithium aluminum hydride, lithium borohydride or sodium borohydride, with a pure optically active compound, such as an amino alcohol, sugar or hydroxyalkaloid. Typically, a chiral reducing agent is about 25% to about 75% (w/w) carbonyl reducing agent and about 25% to about 75% (w/w) optically active compound. A preferred chiral reducing agent for forming the 2S-diastereomer comprises lithium aluminum hydride and (−) quinine. Other suitable chiral reducing agents include 2,5-dimethylborolane, as described in Imai et al., *J. Am. Chem. Soc.*, 108:7402 (1986), K-glucoride, as described in Brown et al., *J. Org. Chem.*, 53:1231 (1988), NB-Enantride, as described in Midland et al.,*J. Org. Chem.*, 56:1068 (1991), borane with a chiral oxazaborolidine catalyst, as described in Corey et al., *J. Am. Chem. Soc.*, 109:7925 (1987), R-Alpine-Hydride, obtainable from Aldrich Chemical Co., and S-Alpine-Hydride, also obtainable from Aldrich Chemical Co.

Alternatively, preferential formation of a diastereomer can occur through the use of a sterically large (or bulky) carbonyl reducing agent.

To preferentially form a diastereomer, a catalytic amount of a chiral reducing agent is mixed with a 3-amino-3-substituted-1-nitro-2-propanol in an organic solvent and then maintained at about −10° C. to about 40° C. to form the preferred diastereomer. A catalytic amount is typically defined as between about 5% and about 50% (w/w) of the 3-amino-3-substituted-1-nitro-2-propanol. Suitable organic solvents include alcohols, esters, ethers and tetrahydrofuran.

During the second reduction, the 1-nitro-3-amino-3-substituted-2-propanol compound, or salt thereof, is then mixed in solution with a nitro reducing agent and is thereby reduced to form a 1,3-diamino-3-substituted-2-propanol chemical intermediate having the structure of structural formula I. During reaction, temperature is maintained between about −40° C. and the reflux temperature of the solvent used. The preferred reaction temperature range is from about 20° C. to about 30° C.

In a preferred embodiment, the nitro reducing agent comprises a hydrogen source in the presence of a hydrogenation catalyst. Suitable hydrogen sources include, for instance, formic acid, soluble formic acid salts, such as ammonium formate, tetrahydronaphthalene and hydrogen. The amount of the hydrogen source used is an amount which will reduce and hydrogenate at least a portion of the 3-amino-3-substituted-2-oxo-1-nitropropane. Typically, the amount of the hydrogen source used is from about 0.1 molar equivalents to about 100 molar equivalents per mole of 1-nitro-3-amino-3-substituted-2-propanol compound.

Hydrogenation catalysts suitable for the second reduction include, for example, palladium on charcoal, palladium hydroxide, platinum black, platinum oxide, a combination of sodium borohydride and nickel chloride, Raney nickel, or a combination of sodium borohydride and cobalt chloride. The amount of catalyst used is typically from about 0.05 molar equivalents to about 10 molar equivalents per mole of 1-nitro-3-amino-3-substituted-2-propanol compound.

Suitable solvents for the solution during the second reduction include organic solvents, such as alcohols, alkanes, benzene, ethers, toluene, tetrahydrofuran, or any combination thereof.

To preclude poisoning of the hydrogenation catalyst by a carbonyl reducing agent containing boron or sulfur, or wherein the 1-nitro-3-amino-3-substituted-2-propanol compound is to be isolated, after the first reduction, the salt of the 1-nitro-3-amino-3-substituted-2-propanol compound is acidified with a suitable aqueous acid to form the 1-nitro-3-amino-3-substituted-2-propanol compound. Suitable acids are those acids which will acidify the salt of the 1-nitro-3-amino-3-substituted-2-propanol compound, but not cleave the protecting group. Suitable acids include, for example, $KHSO_4$, ammonium chloride and citric acid.

Example 7 further describes the reduction of a 1-nitro-3-amino-3-benzyl-2-propanol compound to a 1,3-diamino-3-benzyl-2-propanol (or 1,3-diamino-4-phenyl-2-butanol) chemical intermediate.

In another embodiment, the nitro reducing agent, suitable for the method of this invention, is a chemical or combination of chemicals which will react to reduce and hydrogenate the nitro group to form an amino group. Suitable second reducing agents include, for instance, lithium aluminum hydride. The amount of the nitro reducing agent used is an amount which will reduce and hydrogenate at least a portion of the 1-nitro-3-amino-3-substituted-2-propanol compound. Typically, from about 0.1 moles to about 100 moles of nitro reducing agent are used per mole of 1-nitro-3-amino-3-substituted-2-propanol compound.

It is understood that the 1-nitro-3-amino-3-substituted-2-propanol compound, the nitro reducing agent and the solvent may be combined concurrently, sequentially, or in any order or combination. It is also understood that the 1-nitro-3-amino-3-substituted-2-propanol compound may be added as a solid or in solution. It is further understood the nitro reducing agent may be added as a solid, liquid, gas, slurry, solution or combination thereof.

In an alternate embodiment, 1,3-diamino-3-substituted-2-propanol chemical intermediate is formed via reduction by mixing a 3-amino-3-substituted-2-oxo-1-nitropropane with a third reducing agent, wherein said third reducing agent reduces the carbonyl group and the nitro group to form said chemical intermediate. Suitable third reducing agents include, for instance, lithium aluminum hydride.

The amount of the third reducing agent used is an amount which will reduce at least a portion of the 3-amino-3-substituted-2-oxo-1-nitropropane to form said chemical intermediate. Typically, from about 0.1 moles to about 100 moles of a third reducing agent are used per mole of 3-amino-3-substituted-2-oxo-1-nitropropane.

It is understood that the 3-amino-3-substituted-2-oxo-1-nitropropane, the third reducing agent and the solvent may be combined concurrently, sequentially, or in any order or combination. It is also understood that the 3-amino-3-substituted-2-oxo-1-nitropropane may be added as a solid or in solution. It is further understood the third reducing agent may be added as a solid, liquid, in solution or any combination thereof.

Example 8 further describes the reduction and hydrogenation of a 3-amino-3-benzyl-2-oxo-1-nitropropane compound to form a 1,3-diamino-3-benzyl-2-propanol.

A 3-amino-3-substituted-2-oxo-1-nitropropane compound of the present invention can be produced from an amino acid represented by the following structural formula (structural formula V):

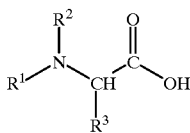

In the method for forming a 3-amino-3-substituted-2-oxo-1-nitropropane compound, said amino acid is mixed with an activating agent and an aprotic solvent under anhydrous conditions to activate said amino acid. An activating agent, as defined herein, is an agent which displaces the hydroxyl of a the carboxyl group of the amino acid with a radical suitable to make the carbonyl carbon of said carboxyl group more susceptible to nucleophilic addition. Examples of suitable activating agents include 1,1'-carbonyldiimidazole (CDI), isobutyl chloroformate, dimethylaminopropylethylcarbodiimide (EDC), dicyclohexyl carbodiimide (DCC) and N-hydroxysuccinimide. For example, wherein CDI is used as activating agent, the hydroxyl group of the amino acid is replaced by an imidazolyl group.

Suitable aprotic solvents include, for instance, methylene chloride, dimethylformamide, tetrahydrofuran, dichloroethane and diethyl ether.

Anhydrous conditions, as defined herein, mean no water is present in the reagents or solvent and that the reaction is performed in an inert atmosphere, such as under argon or nitrogen. Preferably, no free oxygen is present under anhydrous conditions.

It is understood that the amino acid, the activating agent and the solvent may be combined concurrently, sequentially, or in any order or combination. It is also understood that the amino acid may be added as a solid or in solution. It is further understood the activating agent may be added as a solid, liquid or in solution.

Generally, from about 0.1 moles to about 10 moles of activating agent are used per mole of amino acid. A preferred range is from about 1 mole to about 1.5 moles of activating agent per mole of amino acid.

In one embodiment, the amino acid and activating agent are refluxed to drive the reaction to completion. Typically, refluxing is performed for about 0.5 hours to about 4 hours, or until gas evolution subsides.

Further description of the formation of an activated amino acid is provided in Examples 1 and 2.

The activated amino acid is then combined with a nitromethane anion solution under anhydrous conditions to form a reaction mixture, and subsequently the reaction mixture is acidified to form a 3-amino-3-substituted-2-oxo-1-nitropropane compound.

The nitromethane anion solution is formed under anhydrous conditions by mixing an anhydrous base with a nitromethane compound represented by the structural formula (structural formula VI)

$$CHR^4R^5NO_2$$

and optionally an aprotic solvent, such as THF. As the formation of the nitromethane anion solution is typically exothermic, and as salts of nitromethane compounds can be unstable and possibly explosive at higher temperatures, the temperature of the nitromethane anion solution is typically maintained at a cold temperature, such as about 5° C. or less.

Suitable bases are those which will deprotonate the nitromethane compound to form a nitromethane anion. Examples of suitable anhydrous bases include metal alkoxides, such as potassium t-butoxide and sodium methoxide, sodium hydride, sodium bicarbonate and lithium diisopropylamide. The amount of the anhydrous base used is that amount which will deprotonate at least a portion of the nitromethane compound molecules to form nitromethane anions. Typically, from about 0.1 moles to about 1000 moles of anhydrous base are used per mole of nitromethane compound. It is preferred to use from about 1 mole to about 5 moles of anhydrous base per mole of nitromethane compound.

Acids suitable to acidify the reaction mixture consist of acids which will reduce pH to a sufficiently low value to prevent significant enolate formation and to react with remaining nitromethane anions, but will generally not cleave the protecting group from the 3-amino-3-substituted-2-oxo-1-nitropropane. Typically pH is reduced to about 5 or less, with a pH of 2–5 preferred. Suitable acids include, for instance, $H_2SO_4$, HCl, HBr, $H_3PO_4$, $KHSO_4$, citric acid, acetic acid and combinations thereof. Wherein the protecting group is a Boc group, acids where pH is above 3, such as $KHSO_4$, are preferred.

Further description of the formation of 3-amino-3-benzyl-2-oxo-1-nitropropane is described in Examples 1 and 2.

In a further embodiment, a second chemical intermediate is formed from the 1,3-diamino-3-substituted-2-propanol chemical intermediate, wherein the second chemical intermediate is represented by the following structural formula (structural formula VII):

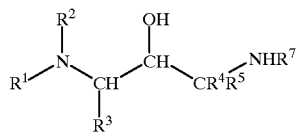

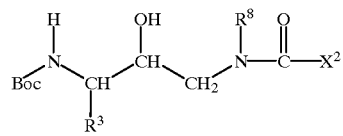

and salts thereof. $R^7$ is selected from the group consisting of alkyl, hydroxyalkyl, alkoxyalkyl, cycloalkylalkyl, heterocycloalkyl, heterocycloalkylalkyl, aryl, heteroaralkyl, and aminoalkyl radicals. Optionally, an aminoalkyl radical may be substituted up to two times with substituents selected from the group consisting of alkyl, cycloalkylalkyl, heterocycloalkyl, heterocycloalkylalkyl, aryl and heteroaralkyl radicals. Furthermore, for a di-substituted aminoalkyl radical, the substituents, combined with the nitrogen atom to which they are bound, may form a heterocycloalkyl or a heteroaryl radical.

To form the second chemical intermediate, a 1,3-diamino-3-substituted-2-propanol is mixed with an $X^1$-$R^7$ compound, where $X^1$ is a halogen radical, such as chloro or bromo, with a base. Suitable bases include bases which generally will not convert the alcohol group to an alkoxide. Preferably, the base is a mild base, such as triethylamine. See Example 9 for further description of the synthesis of 1-N-butyl-3-N-Boc-1,3-diamino-3-benzyl-2-propanol by this method.

Compounds, and pharmaceutical compositions, which can be derived from the second chemical intermediate include the compounds, and pharmaceutical compositions, described in PCT Patent Applications PCT/US91/08593, by Reed et al., and PCT/US93/04806, by Talley et al., the teachings of which are incorporated herein by reference.

In another embodiment a third chemical intermediate is formed from a 3-N-Boc-1,3-diamino-3-substituted-2-propanol, wherein the third chemical intermediate is represented by the following structural formula (structural formula VIII):

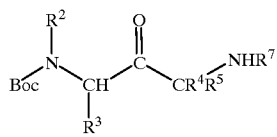

and salts thereof. A 3-N-Boc-1,3-diamino-3-substituted-2-propanol is oxidized via a Swern oxidation, by mixing the 3-N-Boc-1,3-diamino-3-substituted-2-propanol with dimethyl sulfoxide and oxalyl chloride, and then adding a base to form said third chemical intermediate. Suitable bases include bases which generally will not convert the alcohol group to an alkoxide. Preferably, the base is a mild base, such as triethylamine. Compounds, and pharmaceutical compositions, which can be derived from the third chemical intermediate include the compounds, and pharmaceutical compositions, described in U.S. Pat. No. 4,692,455, issued to E. M. Gordon, the teachings of which are incorporated herein by reference.

In yet another embodiment, a first anti-hypotensive compound, and pharmaceutical compositions thereof, can also be formed from a 3-N-Boc-1,3-diamino-3-substituted-2-propanol compound, wherein the anti-hypotensive compound is represented by the following structural formula (structural formula IX):

and salts thereof. $R^8$ is selected from the group consisting of hydrogen, lower alkyl, halo-substituted lower alkyl, alkaryl, heteroaryl and aminoalkyl. $X^2$ is an amino, imino acid or ester radical. Suitable amino, imino acid or ester radicals are further described in U.S. Pat. No. 4,604,402, issued to Godfrey et al., which is incorporated herein by reference.

A first anti-hypotensive compound is formed by mixing a 3-N-Boc-1,3-diamino-3-substituted-2-propanol with Cl—C(O)—$X_2$ in an anhydrous organic aprotic solvent under basic conditions, preferably with an anhydrous base. Suitable bases include bases which generally will not convert the alcohol group to an alkoxide. Preferably, the base is a mild base, such as triethylamine, other alkyl tertiary amines, aryl tertiary amines or pyridines. Anti-hypotensive, and pharmaceutical compositions, which can be produced according to this method include anti-hypotensive compounds, and pharmaceutical compositions thereof, described in U.S. Pat. No. 4,604,402.

In an additional embodiment, a second anti-hypotensive compound, or pharmaceutical compositions thereof, can also be formed from the anti-hypotensive compound of structural formula IX, wherein the second anti-hypotensive compound is represented by the following structural formula (structural formula X):

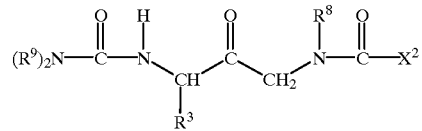

wherein $R^9$ is an alkyl or alkaryl. The compound of structural formula X is the oxidized through Swern oxidation, through mixing with dimethyl sulfoxide and oxalyl chloride, and then adding a weak base, such as triethylamine, to form a compound having the following structural formula (structural formula XI):

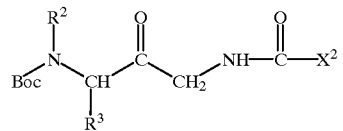

The compound of structural formula XI is then contacted with an acid, such as HCl, HBr or $H_2SO_4$ to cleave the Boc protecting group and form a salt. Subsequently, the salt is mixed with a base, such as triethylamine, and with a Cl—C(O)—N($R^9$)$_2$ to form said anti-hypotensive pharmaceutical composition. Anti-hypotensive agents suitable to be formed by this method are further described in U.S. Pat. No. 4,740,508, issued to Weller et al., which is incorporated herein by reference.

Alternatively, said salt comprises a third chemical intermediate, which can be used to synthesize ureido-keto and hydroxy-substituted ureido compounds as described in U.S. Statutory Invention Registration Number H725, issued to E. M. Gordon.

In another embodiment, a third chemical intermediate is formed from the 1,3-diamino-3-substituted-2-propanol chemical intermediate, wherein the third chemical intermediate is represented by the following structural formula (structural formula XI):

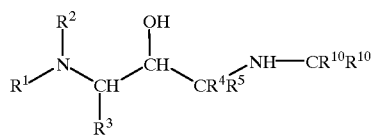

or salts thereof. $R^{10}$ is independently selected from the group consisting of hydrogen, lower alkyl, halo-substituted lower alkyl, aryl and heteroaryl.

In the method for forming the third chemical intermediate, a 1,3-diamino-3-substituted-2-propanol is mixed with an aldehyde or ketone, having the structural formula $R^{10}C(O)R^{10}$ (structural formula XII), in an anhydrous solvent, such as absolute ethanol or toluene, THF, methylene chloride and ethers, to condense the aldehyde/ketone with the 1,3-diamino-3-substituted-2-propanol, thereby forming an imino compound in solution. The imino compound can be isolated but is susceptible to hydrolysis when not retained in solution. The reaction temperature range is typically between about 5° C. and about 40° C.

In a preferred embodiment, a condensation catalyst is added to the 1,3-diamino-3-substituted-2-propanol and aldehyde/ketone to enhance the condensation time and yield of imino compound. Suitable condensation catalysts include, for example, p-toluenesulfonic acid, methanesulfonic and camporsulfonic acid. Typically, the amount of condensation catalyst added is a catalytic amount, for example, about 6.5 to about 10 molar equivalents.

Imino compound solution, within a suitable solvent, is then mixed with an imino reducing agent to cause reductive amination of the imino compound to form a third chemical intermediate having the structure of structural formula XI. The reaction temperature range is typically between about 5° C. and about 35° C. It is preferred that the temperature of the imino reducing agent be between about 0° C. and about 10° C. prior to adding to the imino compound solution in order to make the reaction less energetic.

Examples of suitable solvents include ethanol, toluene, THF, methylene chloride, ethers, acetic acid or an ethanol/acetic acid mixture.

An imino reducing agent, suitable for the method of this invention, is a chemical or combination of chemicals which will reduce and hydrogenate the imino group. Suitable imino reducing agents include, for instance, sodium borohydride, sodium cyanoborohydride, lithium borohydride and lithium aluminum hydride. The amount of imino reducing agent used is an amount which will cause reductive amination of at least a portion of the imino compound molecules contained in solution. From about 0.1 moles to about 100 moles, or more, of imino reducing agent can be used per mole of imino compound. Typically, from about 0.5 to about 5 moles of imino reducing agent are used per mole of imino compound.

In a preferred embodiment, a reductive amination catalyst, such as acetic acid, is also added to the imino compound solution to increase hydrogen generation. Typically the amount of catalyst used is a catalytic amount of about 1–5 wt. %. See Examples 10 and 11 for further descriptions of the formation of third chemical intermediates according to this method.

Compounds, and pharmaceutical compositions, which can be derived from the third chemical intermediate include compounds and pharmaceuticals compositions, described in PCT Patent Applications PCT/US91/08593, by Read et al., and PCT/US93/04806, by Talley et al.

The invention will now be further and specifically described by the following examples.

EXAMPLE 1

Synthesis of 3-N-Boc-amino-3-benzyl-2-oxo-1-nitropropane

In an argon atmosphere and under anhydrous conditions, 2.42 moles (391.8 g) of 1,1'-carbonyl-diimidazole (CDI) and 3 liters of dry THF were mixed in a reactor. 1.89 moles (502.3 g) of Boc-phenylalanine was then added in five portions to the reactor to form a carbonyldiimidazole Boc-phenylalanine solution. Vigorous gas evolution was observed from the reaction. The mixture was refluxed for one hour and subsequently cooled to about 30° C.

In a second reactor, 2.42 moles (272 g) of potassium t-butoxide (t-Bu-O$^-$ K$^+$) and 15 L of THF were mixed and then cooled in an ice bath. Dropwise, 104 mL (2.46 moles; 159.6 g) of 96% nitromethane was added to the ice-cooled t-Bu-O$^-$ K$^+$ solution to form a pale yellow solution.

The carbonyldiimidazole Boc-phenylalanine solution was then added dropwise to said pale yellow solution, which was concurrently cooled in an ice bath, to form a reaction mixture. After the addition, the reaction mixture was allowed to stand at room temperature for 12 hours and then was refluxed for an additional 3 hours to form 3-N-Boc-amino-3-benzyl-2-oxo-1-nitropropane in solution in THF.

After refluxing, the product solution was mixed with a 2.5 L aqueous solution (pH<1) containing 930 g H$_2$SO$_4$ and 530 g KOH to form an organic and an aqueous phase. The organic phase was then concentrated to a paste, while the aqueous phase was then extracted with ethyl acetate. The extracted ethyl acetate and the organic phase's paste were then combined and subsequently washed twice with aqueous KHSO$_4$ (final pH of the aqueous layer was 3) and then dried over anhydrous MgSO$_4$, followed by evaporation of the filtered ethyl acetate, to produce yellow, solid 3-N-Boc-amino-3-benzyl-2-oxo-1-nitropropane. The crude material was subsequently used in Examples 3, 4, 5 and 8 without purification.

An analytical specimen of 3-N-Boc-amino-3-benzyl-2-oxo-1-nitropropane was prepared by recrystallization in ethyl acetate and hexane (2:1) to give a white solid.

$^1$H NMR (300 MHz; CDCl$_3$) shifts observed were 1.40 (s, 9H), 3.0–3.1 (m, 2H), 4.45 (dd, 1H), 4.9 (bd, 1H), 5.30 (dd, 2H) and 7.2–7.4 (m, 5H). The $^{13}$C NMR (75 MHz; CDCl$_3$) shifts observed were 197, 173, 155, 135, 130, 128, 83, 82, 60, 37 and 28. Elemental analysis found percents C 58.42, H 6.51 and N 9.02 with predicted percents of C 58.42, H 6.54 and N 9.09. Melting point observed was 117–118° C.

EXAMPLE 2

Synthesis of 3-N-Cbz-amino-3-benzyl-2-oxo-1-nitropropane 111 mmoles (33.4 g) of Cbz-phenylalanine and 133 mmoles (21.6 g) of CDI were mixed with 600 mL of dry THF in a round bottom flask fitted with a reflux condenser. This mixture was then refluxed for 45 minutes to form a yellow solution.

In a second round bottom flask, 133 mmoles (14.9 g) of potassium t-butoxide, 144 mmoles (9.24 g) of 96% nitromethane and 200 mL of THF were mixed and cooled in an ice bath for 0.5 hours. The yellow solution was then added dropwise via a cannula to the ice-cooled mixture in the second round bottom flask to form a reaction mixture. After the addition, the reaction mixture was allowed to warm to room temperature and was then refluxed for 17 hours to form the 3-N-Cbz-3-amino-3-benzyl-2-oxo-1-nitropropane product in solution. After refluxing, the product solution was brick red and clear. The product solution was allowed to cool to room temperature.

After cooling, the product solution was then mixed with 250 mL of saturated aqueous $KHSO_4$ solution to acidify the mixture and then extracted five times with 100 mL aliquots of ethyl acetate. The ethyl acetate extracts were dried over anhydrous sodium sulfate. Evaporation of the filtered ethyl acetate produced a paste comprising 3-N-Cbz-3-amino-3-benzyl-2-oxo-1-nitropropane.

The 3-N-Cbz-3-amino-3-benzyl-2-oxo-1-nitropropane residue was further purified by recrystallization from ethanol to form an ivory-colored solid.

$^1$H NMR (300 MHz; $CDCl_3$) shifts observed were 3.0–3.2 (m, 2H), 4.0–4.5 (m, 1H), 5.0–5.4 (m, 4H) and 7.2–7.5 (m, 10H). Melting point range 117° C.–121° C.

EXAMPLE 3
Synthesis of 2R,3S and 2S,3S Diastereomers of 3-N-Boc-amino-3-benzyl-1-nitro-2-propanol Using Sodium Borohydride 13.7 mmoles (0.616 g) of 3-N-Boc-amino-3-benzyl-2-oxo-1-nitropropane were dissolved in 70 mL of methanol and cooled to 0° C. Solid $NaBH_4$ (29.8 mmoles; 1.13 g) was then added to this solution to form a reaction mixture. The reaction mixture was allowed to warm to room temperature and then stirred for 14 hours. The methanol was evaporated to yield a white product residue.

The white product residue was then dissolved with 70 mL of water and 70 mL of ethyl acetate to form organic and aqueous phases. $KHSO_4$ (10 g) was also added to acidify the aqueous phase. The phases were then separated by means of a separatory funnel and the aqueous phase was subsequently extracted three times with 50 mL aliquots of ethyl acetate. The organic phases were combined, dried over anhydrous sodium sulfate, filtered and then evaporated to remove the ethyl acetate solvent and produce crude 3-N-Boc-amino-3-benzyl-1-nitro-2-propanol.

The crude product was then purified by flash chromatography on a silica gel column using 5:1 hexane/ethyl acetate. The fractions containing the desired diastereomers were separately pooled and the solvent was evaporated from each to leave a white residues.

The fraction ($R_f$=0.20) corresponding to the (2R,3S) diastereomer was the minor fraction, with a yield of about 13%.

$^1$H NMR (300 MHz, $CDCl_3$) shifts observed were 1.6 (s, 9H), 2.9–3.0 (m, 2H), 3.3–3.4 (m, 2H), 3.8–3.9 (m, 1H), 4.3–4.4 (m, 1H), 4.5–4.6 (m, 2H), 4.9–5.0 (m, 1H) and 7.2–7.4 (m, 5H).

The fraction ($R_f$=0.16) corresponding to the (2S,3S) diastereomer was the primary fraction, with a yield of about 37%. $^1$H NMR (300 MHz, $CDCl_3$) shifts observed were 1.3 (s, 9H), 2.8 (dd, 1H), 3.15 (dd, 1H), 3.85 (m, 1H), 4.4 (m, 1H), 4.5 (t, 1H), 4.8 (d, 1H), 5.0 (d, 1H), 6.05 (bd, 1H) and 7.2–7.3 (m, 5H). The $^{13}$C (75 MHz, Acetone-$d_6$) shifts observed were 156, 140, 132, 130, 127, 82, 80, 73, 57, 37 and 28. Elemental analysis found percentages were C 57.91, H 7.18 and N 9.02 with predicted percentages of C 58.04, H 7.15 and N 9.03. Melting point observed was 144–144.5° C.

EXAMPLE 4
Synthesis of 3-N-Boc-amino-3-benzyl-1-nitro-2-propanol Using Lithium tri-(sec-butyl)borohydride 4.05 mmoles (1.25 g) of 3-N-Boc-amino-3-benzyl-2-oxo-1-nitropropane were dissolved in 100 mL of dry THF and cooled to 0° C. in an ice bath, under argon and with continuous stirring. Six mLs of 1 M lithium tri-(sec-butyl) borohydride solution in dry THF were then added dropwise to form a reaction mixture. The reaction mixture was then maintained at 0° C. for 2 hours. During the 2 hour reaction period, a minor amount of gas evolved from the reaction mixture and a light yellow color appeared. After 2 hours, the reaction was quenched by adding about 1 mL of acetone while still at 0° C.

The product residue was then mixed with 50 mL of ethyl acetate and 50 mL of 10% aqueous $KHSO_4$ solution to form organic and aqueous phases and to acidify these phases. The phases were then transferred into a separatory funnel with an additional 25 mL of ethyl acetate for rinsing and then separated. The aqueous phase was subsequently re-extracted once with a 75 mL aliquot of ethyl acetate. The organic phases were combined, washed once with brine, dried over anhydrous sodium sulfate and then evaporated by means of a rotary evaporator to form a yellow oil.

The ratio of (2R,3S) and (2S,3S) diastereomers was found to be 1:1 by NMR analysis.

EXAMPLE 5
Synthesis of 3-N-Boc-amino-3-benzyl-1-nitro-2-propanol Using Lithium tri-tert-butoxyaluminohydride 5.51 mmoles (1.70 g) of 3-N-Boc-amino-3-benzyl-2-oxo-1-nitropropane were dissolved in 100 mL of dry THF and cooled to 0° C. in an ice bath, under argon and with continuous stirring. Nine mLs of 1 M lithium tri-tert-butoxyaluminohydride solution in dry THF were then added to form a reaction mixture. A pale yellow color appeared. The reaction mixture was then maintained at 0° C. for 2.15 hours.

The reaction was then quenched by adding 50 mL of 10% aqueous $KHSO_4$ solution while still at 0° C. Upon addition, a minor amount of gas evolved from the reaction mixture and aluminum salts precipitated from solution.

The product residue was then transferred to a separatory funnel with 100 mL of ethyl acetate to form organic and aqueous phases. The phases were separated and then the aqueous phase was subsequently extracted once with a 50 mL aliquot of ethyl acetate. The organic phases were combined, washed once with brine, dried over anhydrous sodium sulfate and then evaporated by means of a rotary evaporator to from a white solid.

The ratio of (2R,3S) and (2S,3S) diastereomers was found to be 1:3 by NMR analysis.

EXAMPLE 6
Synthesis of 3-N-Cbz-amino-3-benzyl-1-nitro-2-propanol

To one gram of 3-N-Cbz-amino-3-benzyl-2-oxo-1-nitropropane, dissolved in 30 mL of methanol, was added 0.21 g of $NaBH_4$ to form a reaction mixture. The reaction mixture was allowed to stand at room temperature and then stirred for 4 hours. The methanol was evaporated under reduced pressure to yield a product residue.

The product residue was then mixed with 5 mL of aqueous saturated ammonium chloride solution and extracted twice with 30 mL of aliquots of ethyl acetate to form organic and aqueous phases. The phases were then separated by means of a separatory funnel. The organic phase was dried over anhydrous magnesium sulfate, filtered and then evaporated to remove the ethyl acetate solvent and produce a fluffy white solid.

The ratio of (2R,3S) and (2S,3S) diastereomers was found to be 18:70 by NMR analysis.

EXAMPLE 7
Synthesis of 3-N-Boc-1,3-diamino-3-benzyl-2-propanol Using Ammonium Formate To 14.5 g of 3-N-Boc-amino-3-benzyl-1-nitro-2-propanol, dissolved in 150 mL of anhydrous methanol and under argon, was added 1.1 g of Pd/C (5%) catalyst. Ammonium formate (28.1 g) was then added in one portion. An additional 250 mL of methanol was subsequently added to facilitate stirring. The mixture was then stirred overnight.

The reaction mixture was then filtered to remove precipitates of ammonium formate. The filtrate was then concentrated to give a white solid.

$^1$H NMR (300 MHz, Acetone-$d_6$ DMSO) shifts observed were 1.40 (s, 9H), 2.80 (dd, 1H), 2.95–3.05 (m, 3H), 3.15–3.25 (m, 2H), 3.70 (m, 1H), 3.80 (m, 1H), 7.20–7.30 (m, 5H) and 8.20 (s, 2H). Melting point observed was 134–136° C.

EXAMPLE 8
Synthesis of 3-N-Boc-1,3-diamino-3-benzyl-2-propanol Using Lithium Aluminum Hydride 2.92 mmoles (1 g) of 3-N-Boc-amino-3-benzyl-2-oxo-1-nitropropane were dissolved in dry THF and cooled to 0° C. in an ice bath, under argon and with continuous stirring. 11.7 mmoles (0.44 g) of lithium aluminum hydride, dissolved in THF, was added. After gas evolution subsided, the mixture was refluxed for 3 hours and then maintained at room temperature to yield a cloudy solution. Concentrated HCl (4 mL) was then added to make the solution clear. The solution was then extracted with 200 mL of methylene chloride. The combined organic layers were washed with 150 mL of saturated sodium bicarbonate and then dried over magnesium sulfate to yield the product.

EXAMPLE 9
Synthesis of 1-N-butyl-3-N-Boc-1,3-diamino-3-benzyl-2-propanol 1.12 g of 3-N-Boc-1,3-diamino-3-benzyl-2-propanol were dissolved in 7 mL of dimethylformamide. To this solution was added 0.54 g (3.9 mmole) 1-bromobutane dropwise. The resulting solution was maintained at 80° C. for 5 hours and then cooled to room temperature before dilution with 50 mL of ethyl ether. The resulting solution was washed with two 20 mL aliquots of water. The organic phase was dried (MgSO$_4$) and concentrated to afford a solid. Column chromatography of the crude product produced 1-N-butyl-3-N-Boc-1,3-diamino-3-benzyl-2-propanol.

EXAMPLE 10
Synthesis of Amino Alcohol from N-t-Boc-L-proline

In a 25 Ml round bottom flask flushed with argon, N-t-Boc-L-proline (1.0 g, 4.6 mmole) was stirred with anhydrous tetrahydrofuran (4.0 Ml) for 10 minutes. A very clear colorless solution was obtained. To this solution, 1,1'-carbonyldiimidazole (0.75 g, 4.6 mmole) was added under argon, and a lot of gas evolution was observed. The resulting clear solution was stirred at room temperature for 4 hours to form an activated ester.

In another round bottom flask, potassium t-butoxide (0.55 g, 4.6 mmole) was dissolved in 3.0 Ml tetrahydrofuran and cooled to 0–5° C. in an ice-bath. A clear solution was obtained. Then nitromethane (0.3 Ml, 5.5 mmole) was added slowly with a lot of precipitate formation. The slurry was stirred for 20 minutes, and then the activated ester solution was transferred to the nitromethane anion slurry by a syringe. The resulting slurry was stirred at room temperature overnight.

The slurry became bright yellow color and TLC (CH$_2$Cl$_2$:MeOH:NH$_4$OH=100:10:2, UV+ninhydrin) indicated the completion of the reaction. The reaction mixture was acidified to pH 2–3 with 1N HCl, then extracted twice with ethyl acetate. The combined organic solutions were dried over magnesium sulfate, filtered and evaporated to dryness to give the desired product with quantitative yield as yellow solid. $^1$H NMR confirmed the structure with good purity. The experiment was repeated at 10 g scale and produced the same result.

Nitro alcohol from N-t-Boc-L-proline was made by sodium borohydride reduction under varying conditions. First it was carried out in ethanol in an ice-bath with 1 equivalent of NaBH$_4$. The internal temperature went up to 31° C. The mixture was stirred overnight. The reaction was worked up by acidifying to pH 3 with 1N HCl, then extracting with ethyl acetate. TLC showed at least six spots. Crystallization of the crude product failed. The product was then purified on a silica gel column flushed with ethyl acetate followed by 10% methanol in ethyl acetate. The produce was re-columned on silica gel flushed with ethyl acetate/hexane 1/3. The desired product was obtained as light oil. TLC showed two spots for the diastereomers.

The reaction was repeated in ethanol. The temperature was controlled below 5° C. and 1.5 equivalents of NaBH$_4$ was used. TLC showed a clean but incomplete reaction (two spots for the diastereomers). A preparative TLC (5% methanol in methylene chloride) was carried out and pure product was obtained as diastereomers.

The reaction was also carried out in methanol instead of ethanol below 10° C. Again this was a clean reaction. Efforts were made to push the reaction to completion, but even with 10.5 equivalents of NABH$_4$ and 30 hours of stirring, it remained incomplete.

To push the reaction to completion, the nitro ketone was refluxed in ethanol/THF 1/1. The reaction was completed but did not give the desired nitro alcohol. The product of this reaction was unidentified.

The hydrogenation of the nitro alcohol was first carried out in a Parr-Shaker. 1.4 g Nitro alcohol was dissolved in 90 Ml of methanol. 140 mg of 5% palladium on activated carbon was used as the catalyst. The hydrogenation was done at 40 psi. After 18 hours, the reaction was very incomplete. So the reaction mixture was transferred to a round bottom flask and concentrated to 20 Ml. 230 mg 10% Pd/C was added and the hydrogenation was continued using a hydrogen balloon. The reaction was completed in 24 hours. The catalyst was filtered and the crude product was purified by a silica gel column. The product was obtained as unseparated diastereomers.

The compounds described in this example are illustrated structurally below.

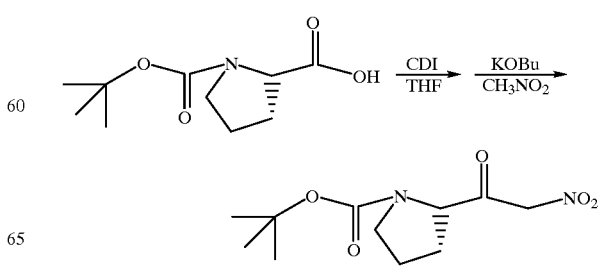

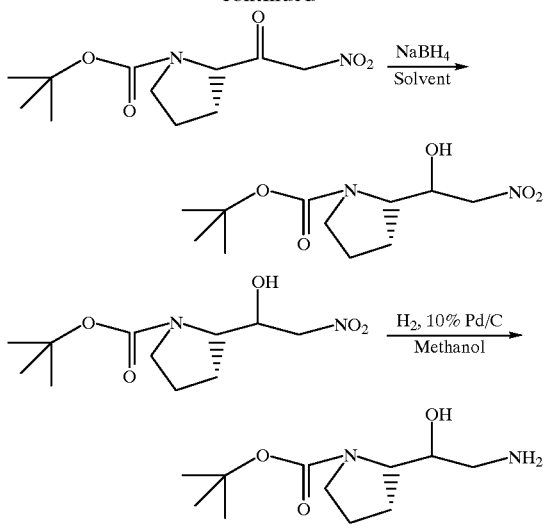

EXAMPLE 11

Synthesis of Amino Alcohol from N-t-Boc-L-lysine.

Nα, Nε-Di-t-Boc-L-lysine was bought as dicyclohexylammonium salt. The salt was acidified to pH 102 with 1N HCl then extracted with ethyl acetate. The ethyl acetate solution was dried and evaporated to dryness to give the protected lysine as the free acid. The synthesis of the nitro ketone was basically the same as the protected proline. The product was obtained as yellow solid with a yield of 88.4%. $^1$H NMR confirmed with structure.

The nitro ketone (1.41 g, 3.62 mmole) was dissolved in 25 Ml methanol and cooled in an ice-bath. Then sodium borohydride (1.42 g, 37.6 mmole) was added very slowly in small portions to keep the temperature below 0° C. The reaction was completed in 2 h. The mixture was then diluted with water and ethyl acetate, acidified to pH 3 with 1N HCl and two layers were separated. The aqueous layer was extracted with ethyl acetate and the combined organic layers were dried over magnesium sulfate, filtered and evaporated to dryness. The crude product was purified on silica gel column flush with $CH_2Cl_2$:MeOH:$Et_3N$ 100:5:1. The product was obtained as off-white solid of diastereomers with a yield of 74.8%. $^1$H NMR and IR confirmed the structure.

The sodium borohydride reduction was repeated at 2.0 g scale and quantitative yield was obtained. $^1$H NMR and TLC ($Ch_2Cl_2$:MeOH;$Et_3N$ 100:5:1 or $CH_2Cl_2$:EtOAc 1:1) were exactly the same as the above column purified product. The crude product was used in the next step without further purification.

In a round bottom flask, nitro alcohol (crude, 2.8 g, 7.16 mmole) was dissolved in 35 Ml methanol. 0.56 g 10% Palladium on activated carbon was added and the hydrogenation was carried out under a hydrogen balloon atmosphere. The reaction was completed in 16 hours. The catalyst was filtered off and the filtrate was evaporated to dryness to give 1.74 g of an off-white solid. $^1$H NMR confirmed the structure, and TLC ($CH_2Cl_2$:MeOH:$Et_3N$ 100:5:2 ninhydrine) showed only trace amount of impurity. Further purification was not done.

The compounds described in this example are illustrated structurally below.

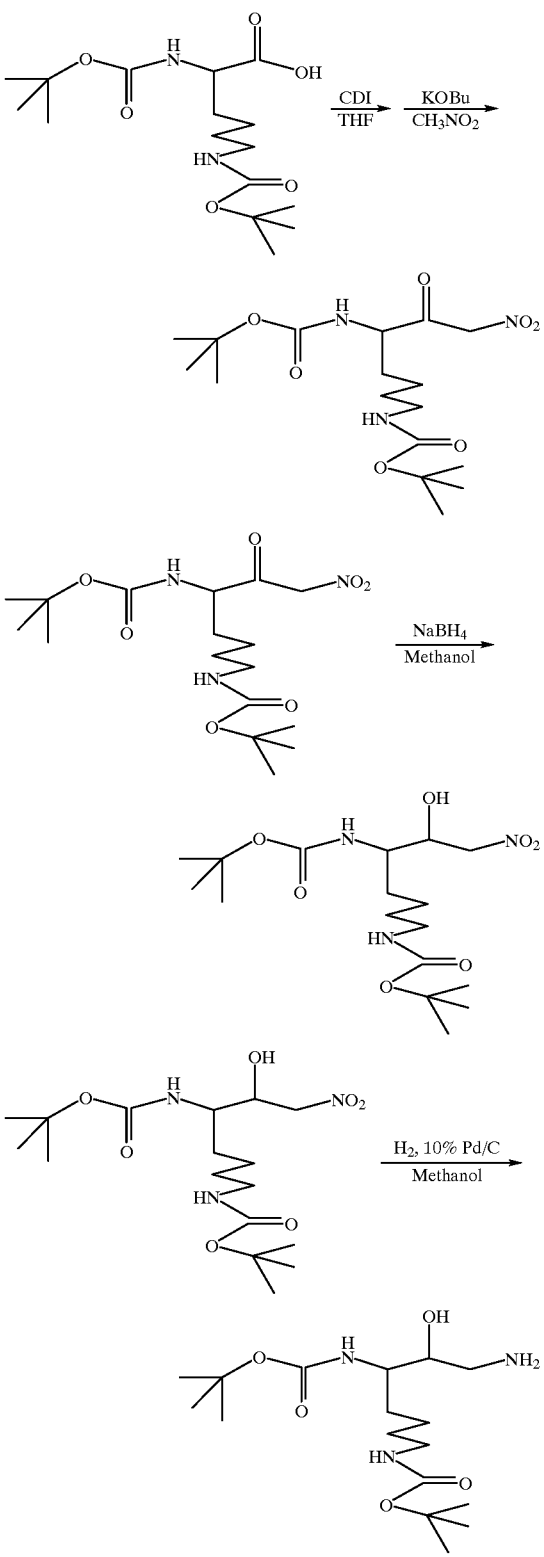

EXAMPLE 12

Synthesis of Amino Alcohol from N-t-Boc-L-hydroxyproline

N-t-Boc-L-hydroxy proline was given as the dicyclohexylammonium salt. The salt was acidified to pH 3 with 1N HCl and extracted with CH₂Cl₂ and ethyl acetate. In general, only ethyl acetate should be used for extraction as it was later found that methylene chloride could dissolve some of the dicyclohexylammonium chloride. The organic extractions were dried over magnesium sulfate, filtered and evaporated to dryness to give the free acid.

The synthesis of the nitro ketone was basically the same as the protected proline. The product was obtained as yellow solid. $^1$H NMR confirmed the structure, but TLC showed either a long strip or a few continuous spots, indicating that the product was not quite pure. GC-Mass was used to get the molecular weight, but no results were obtained due to probable decomposition on the GC column. The crude product was not further purified.

The crude nitro ketone was reduced by sodium borohydride in ethanol at the temperature below 10° C. 10 Equiv. of sodium borohydride was used. Yellow oily solid was obtained. TLC of the crude product was not very clear. $^1$H NMR was not clean, resulting in difficulty detecting product.

Potentially, the hydroxy group in N-t-BOC-L-hydroxy proline could be protected with a benzyl group to make the nitro ketone and nitro alcohol form. In the final step the benzyl group is cleaved by hydrogenation.

The compounds described in this example are illustrated structurally below.

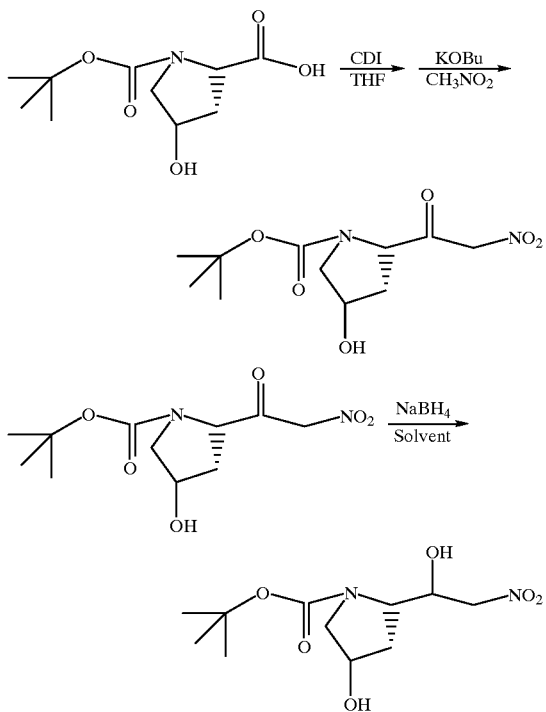

EXAMPLE 13
Synthesis of Amino Alcohol from N-t-Boc-L-isoleucine

The preparation of the nitro ketone was basically the same as the synthesis of the nitro ketone from M-t-Boc-L-lysine. Bright yellow oil was obtained at a quantitative yield. The oil solidified later on high vacuum. $^1$H NMR confirmed the structure. TLC (CH₂Cl₂:MeOH:NH₄OH-100:10:2) showed trace amount of impurity. The product was used in the next step without further purification.

The nitro alcohol was prepared by sodium borohydride reduction. The nitro ketone (2.35 g, 8.47 mmole) was dissolved in 20 Ml of methane and the solution was cooled in an ice-bath. To the yellow solution, sodium borohydride (3.37 g, 86 mmole) was added very slowly in small portions to keep the temperature below 10° C. The total addition time was 3 hours. The resultant slurry was stirred for 6 hours, and the reaction was still incomplete. The reaction was worked up by acifying to pH 2 with 1N HCl and extracting with ethyl acetate twice. The combined ethyl acetate extractions were dried over magnesium sulfate, filtered and evaporated to dryness to give the crude product. The crude product was purified on a column twice (solvent system: CH2Cl2:EtOAc=5:1) but both times the nitro ketone at the baseline came out together with the nitro alcohol. The product was then stirred with sodium bicarbonate for half hour (because the nitro ketone was more acidic than the nitro alcohol, this removed the nitro ketone from the organic layer to the aqueous layer), then extracted with methylene chloride. The methylene chloride solution was dried over magnesium sulfate, filtered and evaporated to dryness to give the desired product. $^1$H NMR confirmed the structure, and TLC showed only trace amount of residual nitro ketone. The yield was low (33%), probably because the sodium bicarbonate also removed some of the nitro alcohol to the aqueous layer.

Hydrogenation was done in methanol under hydrogen atmosphere. In a round bottom flask, the nitro alcohol from isoleucine (730 mg) was dissolved in 15 Ml of methanol. 150 mg 10% Pd/c was wet with 4 Ml of ethanol and transferred to the flask. The flask was evacuated three times, filled with hydrogen (balloon) and allowed to stir overnight to complete hydrogenation. The amino alcohol was obtained, and both $^1$H NMR and $^{13}$CNMR confirmed the structure.

The compounds described in this example are illustrated structurally below.

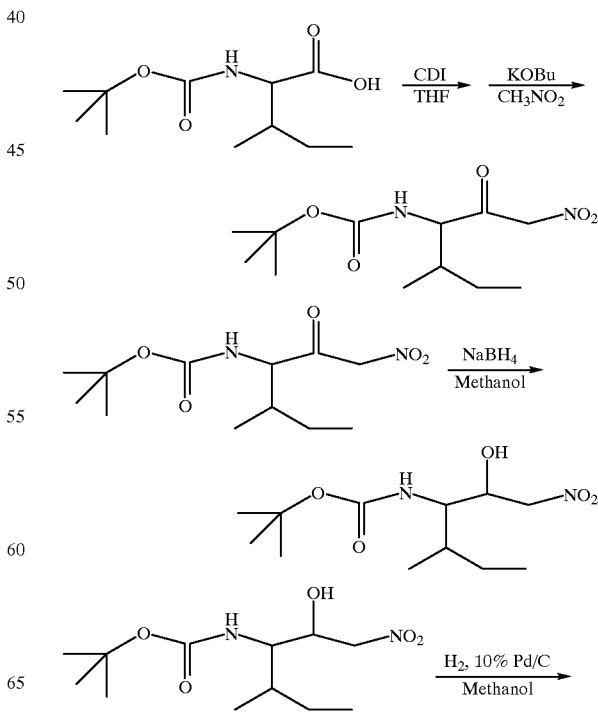

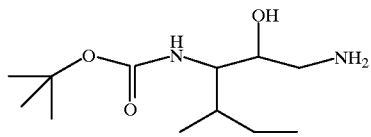

EXAMPLE 14
Synthesis of Amino Alcohol from N-t-Boc-O-benzyl-L-tyrosine

The synthesis of the nitro ketone was basically the same as the preparation of the nitro ketone from N-t-BOC-L-proline. The reaction was done twice and both trials gave the desired nitro ketone with reasonable purity (from NMR). The product was used in the next step without further purification.

The reduction of the nitro ketone by sodium borohydride was unexpected. In the first trial, the reduction was done in methanol with 10 equivalents of $NABH_4$. The temperature was kept below 10° C. The reaction was worked up by acidifying to pH 1 with 1N HCl, then basifying to pH 11 with 1N NaOH. Basification should not be carried out, however, as it was later determined that basifing to pH 11 may deprotonate the methylene group next to the nitro group. The solution was extracted with ethyl acetate three times, and the combined ethyl acetate extracts were dried over magnesium sulfate, filtered and evaporated to dryness to give the crude product as a pale yellow solid. The crude product was purified on a silica gel column flushed with 5% methanol in methylene chloride. Pure product (diastereomers) was obtained at 55% yield. $^1$H NMR and IR confirmed that the desired nitro alcohol was prepared.

In the second trial, the reduction was done in ethanol with 10 equivalents of $NaBH_4$. The temperature remained at 4° C. throughout the addition of $NaBH_4$. The reaction was worked up by acidifying to pH 1 with 1N HCl, then basifying to pH 11 with 1N NaOH. The solution was extracted twice with ethyl acetate. The combined extracts were dried over magnesium sulfate, filtered and evaporated to dryness to give the crude product. The aqueous layer was acidified to pH 4 and re-extracted with ethyl acetate. The extract was dried over $MgSO_4$, filtered and evaporated to dryness and combined with the above product. TLC (5% methanol in methylene chloride) showed only trace amounts of the expected nitro alcohol (by co-spotting with the nitro alcohol obtained in methanol reduction). The major product was the spot below the nitro alcohol. This unexpected product was purified on a silica gel column flushed with 5% methanol in methylene chloride. Pure sample was obtained, and $^1$H NMR showed there was no nitro methylene signal at 4.5 ppm (typical chemical shift for nitro alcohol). $^{13}$C NMR was also done and the carbon next to the nitro group was missing. Elemental analysis suggested a molecular formula of $C_{21}H_{27}N_1O_4$. Since the BOC group was on from NMR, the nitro methylene was removed. Mass spectra results confirmed that the nitro methylene was cleaved from the molecule. The molecular weight was found to be 357, which confirmed the suggested structure.

Unexpectedly, a primary alcohol was obtained instead of the desired nitro alcohol. The mechanism of the removal of the nitro methylene is unknown.

Hydrogenation of the nitro alcohol from the protected tyrosine was carried out. In a 50 Ml round bottom flask, nitro alcohol (190 mg) was dissolved in 3 Ml of methanol. 40 mg 10% Pd/C was taken up in 2 Ml of methanol and then transferred to the nitro alcohol solution. The flask was evacuated, filled with hydrogen (balloon) and allowed to stir overnight. TLC indicated the completion of the hydrogenation. The solution was filtered through celite and evaporated to dryness. 120 mg product (89% yield) was obtained. Surprisingly, no amino alcohol was obtained. $^1$H NMC and $^{13}$CNMR confirmed that the nitro methylene was cleaved. The benzyl group was also cleaved as expected. Thus, the product from this hydrogenation was not the expected amino alcohol, but the primary alcohol without the benzyl group was obtained.

The hydrogenation of the primary alcohol (with benzyl group) was also carried out. The substrate (200 mg) was dissolved in 2 Ml of methanol. 40 mg 10% Pd/C was taken up in 2 Ml of methanol and transferred into the substrate solution. The flask was evacuated with vacuum, filled with hydrogen (balloon) and allowed to stir overnight. The solution was filtered through celite and evaporated to dryness. $^1$H NMR suggested that the benzyl group was cleaved and the same product as the hydrogenation of the nitro alcohol was obtained.

Even though the nitro alcohol was obtained in the methanol $NaBH_4$ reduction, it did not give the desired amino alcohol in the hydrogenation. Instead, the nitro methylene group was cleaved during hydrogenation for reasons which are unclear.

The compounds described in this example are illustrated structurally below.

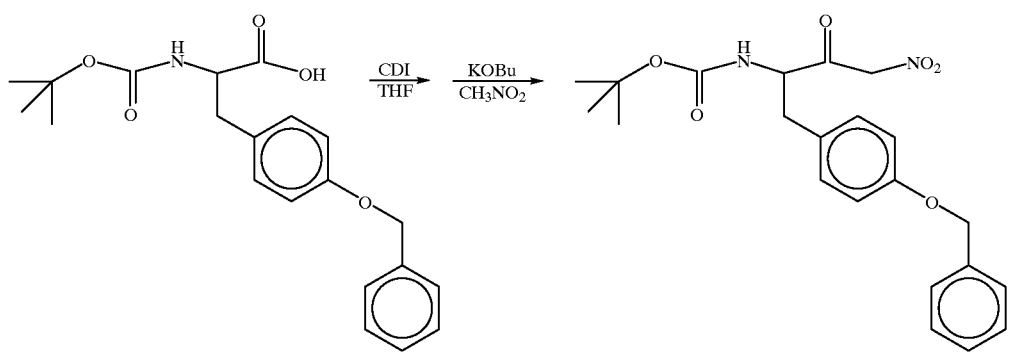

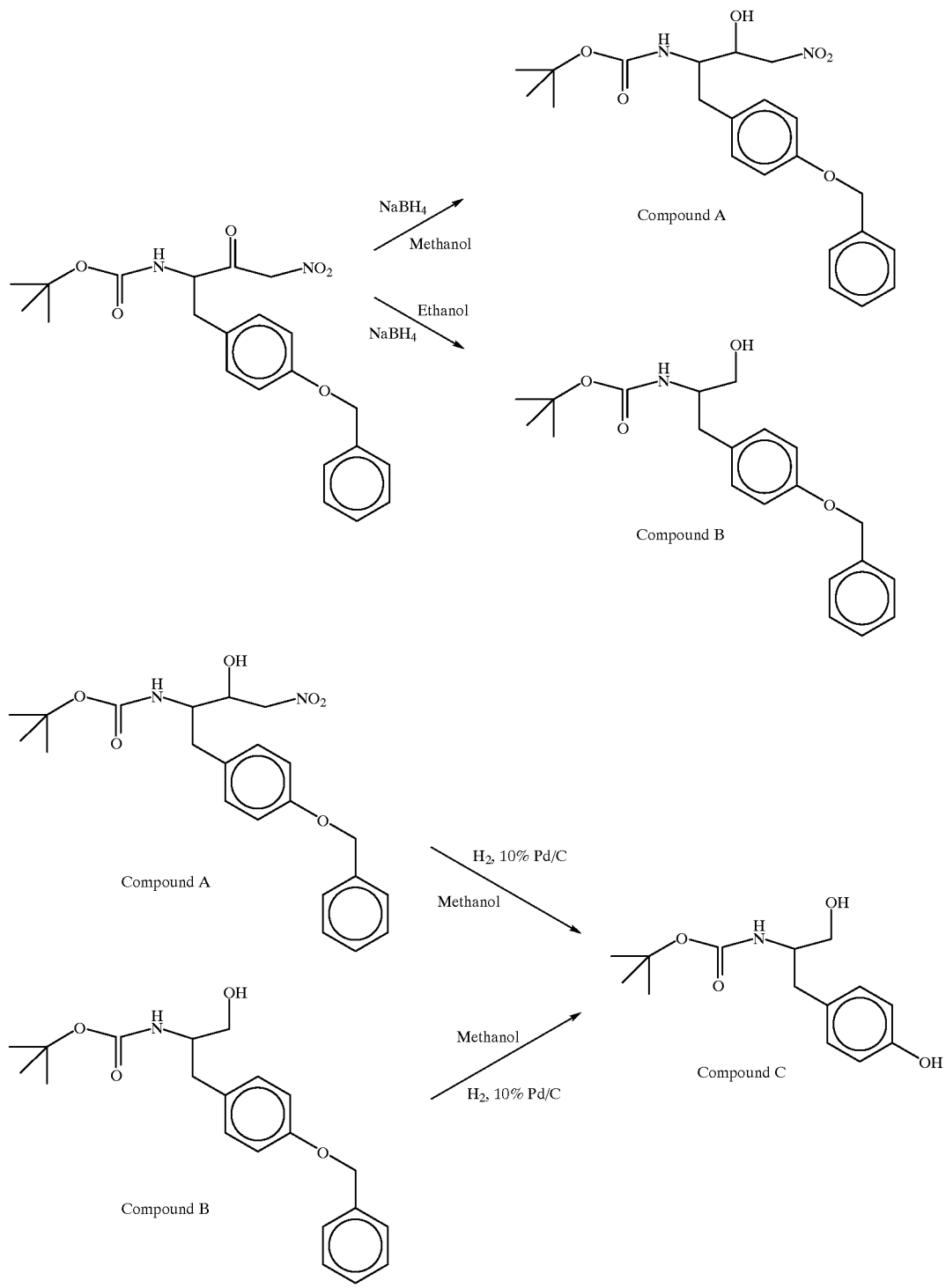

EXAMPLE 15
Synthesis of Amino Alcohol from N-t-Boc-O-benzyl-L-threonine

The synthesis of the nitro ketone was basically the same as that of the N-t-BOC-L-proline. A dark yellow oil was obtained as the crude product. In the $^1$H NMR of the crude product, a set of peaks was observed at 5.5 ppm which was assigned to the benzyl methylene group. The typical nitro methylene group was not seen at 5.5 ppm, but instead appeared at 4.5 ppm as a doublet of doublet. Presumably the product was obtained, it was used in the next step without further purification.

Sodium borohydride reduction was carried out on the nitro ketone prepared in the first step. In a round bottom flask, the nitro ketone (1.35 g, 3.83 mmole) was dissolved in 43 Ml of methanol. The solution was cooled in an ice-bath. Then sodium borohydride (1.52 g, 40.2 mmole) was added slowly over 35 minutes. The temperature was maintained below 10° C. for most of the time except a couple of occasions on which NaBH$_4$ was added in a large amount accidentally and the temperature jumped to 35° C. The reaction was worked up by acidifying to pH 2 with 1N HCl then extracting twice with ethyl acetate. The combined EtOAc extracts were dried over MgSO$_4$, filtered and evaporated to dryness to give the crude product. Column purification was carried out twice but failed. The nitro ketone at the baseline repeatedly came out together with the product. The product was then dissolved in methylene chloride, stirred with saturated sodium bicarbonate for one hour, and the two layers were separated. The methylene chloride solution was dried over MgSO$_4$, filtered and evaporated to dryness to give a fairly pure product (380 mg).

The compounds described in this example are illustrated structurally below.

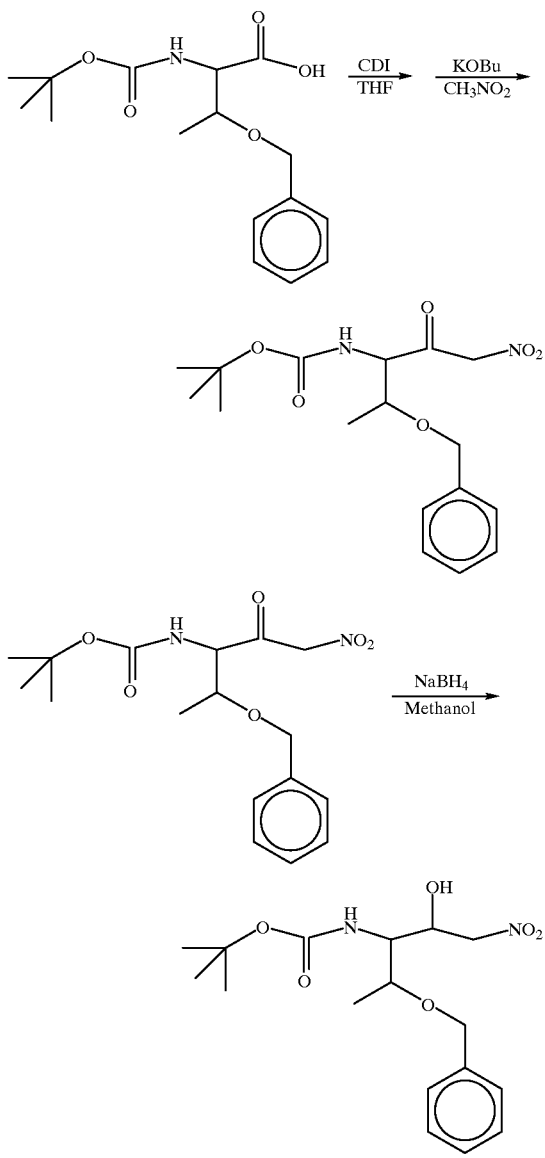

EXAMPLE 16
Synthesis of (2S,3S)-3-N-Boc-1-N-(4-methoxybenzyl-3-benzyl-2-propanol 3.57 mmoles (0.49 g) of p-anis aldehyde was added to 1.79 mmol (0.50 g) of 3-N-Boc-1,3-diamino-3-benzyl-2-propanol, which was dissolved in 5 ml of ethanol (abs.) to form a reaction mixture. The reaction mixture was then stirred at room temperature overnight. Subsequently, 2.65 mmol (100 mg) of sodium borohydride, at 0° C., was added to the reaction mixture, in several portions. The reaction mixture was then stirred for another 3 hours and allowed to return to room temperature. 5 ml of saturated NH$_4$Cl solution was then added to the reaction mixture. The resulting mixture was then extracted twice with 20 mL aliquots of ethyl acetate. The ethyl acetate extract was washed with water and brine, then dried over anhydrons sodium sulfate, filtered and then evaporated to remove the solvent and to produce a crude product. The crude product was purified by flash chromatography on a silica gel column using methanol/hexane (1% methanol in hexane). 0.5 g of (2S,3S)-3-N-Boc-1-N-(4-methoxy benzyl). 1,3-diamino-3-benzyl-2-propanol was obtained (70% in yield).

$^1$H NMR (300 MHz, CDCl$_3$) shifts observed were 7.5–7.30 (7H, m), 6.85–6.90 (2H, m), 4.80–4.90 (1H, m), 3.85 (3H, s), 3.70–3.80 (3H, m), 3.50–3.60 (1H, m), 3.40 (2H, bd) 2.95–3.05 (1H, m), 2.60–2.90 (3H, m), 135 (9H, s). Elemental analysis found percentages were C 68.26, H 8.05, N 7.19 with predicted percentages of C 68.94, H 7.92, N 6.99.

EXAMPLE 17
Synthesis of (2S,3S)-3-N-Boc-1N-isobutyl-1, 3-diamino-3-benzyl-2-propanol To 3.57 mmol (1.00 g) 3-N-Boc-1,3-diamino-3-benzyl-2-propanol, which was dissolved in 25 mL of ethanol (abs.), was added 10.6 mmol (0.77 g) of isobutyraldehyde, forming a reaction mixture. The mixture was then stirred overnight at room temperature.

To the above reaction mixture, 0.5 ml acetic acid was added at 0° C., followed by addition of 4.00 mmol (0.15 g) of sodium borohydzide in portions. Subsequently, the mixture then was stirred for another 6 hours and allowed to return to room temperature.

Ten (10) ml of saturated NH$_4$Cl solution was added to the reaction mixture which then was extracted twice with 20 ml aliquots of ethyl acetate. The ethyl acetate extract was washed with water and brine, dried over sodium sulfate, filtered and then evaporated to remove the solvent thereby producing a white residue. Recrystallization in 15 ml EtoAc 1.5 ml hexane gave 0.97 g of (2S, 3S)-3-N-Boc-1-N-isobutyl-1,3-diamino-3-benzyl-2-propanol (80% in yield).

$^1$H NMR (300 MHz, CDCl$_3$) shifts observed were 7.5–7.30 (5H, m), 4.70 (1H, m), 3.60–3.70 (1H, bd), 3.45–3.55 (1H, bd), 3.0–3.1 (1H, dd), 2.85–2.95 (1H, m), 2.65–2.80 (2H, m), 3.30–2.50 (2H, m), 1.75–1.85 (1H, m), 1.35 (9H, s) 1.00 (6H, d). Elemental analysis found percentages were C 67.28, H 9.38, N 8.13 with predicted percentages of C 67.85, H 9.54, N 8.36.

Chemical Analysis

Melting points were determined with a Thomas Hoover capillary melting point apparatus and are uncorrected. Elemental analyses were performed by Atlantic Microlab, Inc., Norcross, Ga. $^1$H NMR spectra were measured at 300 MHz on a Bruker AC300 and $^{13}$C NMR spectra were measured at 75 MHz obtained on a Bruker AC300.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A method for preferentially forming a (2S) 1-nitro-3-amino-3-substituted-2-propanol chemical intermediate represented by the formula

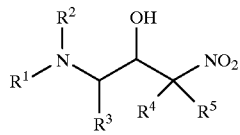

or salts thereof, wherein:
- $R^1$ is an amino protecting group;
- $R^2$ is selected from the group consisting of —H, C1–C18 alkyl, aryl, acetyl and tosyl;
- $R^3$ is a side-chain of an α-amino acid; and
- $R^4$ and $R^5$ are each independently selected from the group consisting of —H, alkyl, aryl, nitrile and alkoxycarbonyl, comprising the step of contacting a 3-amino-3-substituted-2-oxo-1-nitropropane having the structural formula

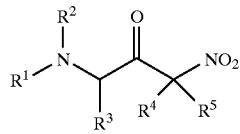

with at least one reducing agent that will reduce the carbonyl to preferentially form a 2S diastereomer, thereby reducing said 3-amino-3-substituted-2-oxo-1-nitropropane to preferentially form said (2S) 1-nitro-3-amino-3-substituted-2-propanol chemical intermediate.

2. A method of claim 1 wherein said reducing agent includes a sterically large carbonyl reducing agent.

3. A method of claim 1 wherein $R^1$ is selected from the group consisting of benzyl, benzyloxycarbonyl and 9-fluorenylmethoxycarbonyl.

4. A method of claim 1, further comprising the step of contacting said 1-nitro-3-amino-3-substituted-2-propanol, with a nitro reducing agent, thereby forming said 1,3-diamino-3-substituted-2-propanol compound.

5. A method of claim 4 wherein said nitro reducing agent comprises a hydrogen source in the presence of a hydrogenation catalyst.

6. A method of claim 5 wherein said hydrogen source is selected from the group consisting of hydrogen, formic acid and a formate salt.

7. A method of claim 6 wherein said formate salt comprises ammonium formate.

8. A method of claim 5 wherein said hydrogenation catalyst is selected from the group consisting of palladium on charcoal, palladium hydroxide, platinum black, platinum oxide, a combination of sodium borohydride and nickel chloride, and a combination of sodium borohydride and cobalt chloride.

9. A method of claim 1 wherein said 3-amino-3-substituted-2-oxo-1-nitropropane is formed by a method comprising the steps of:
   a) contacting an α-amino acid with an activating agent and an aprotic solvent under anhydrous conditions to form an activated amino acid;
   b) contacting said activated amino acid with a nitromethane anion solution under anhydrous conditions to form a reaction mixture; and
   c) adding an acid with the reaction mixture to form said 3-amino-3-substituted-2-oxo-1-nitropropane.

10. A method of claim 9 for forming an nitromethane anion solution, further comprising the step of mixing a anhydrous base with a nitromethane compound to form a nitromethane anion solution.

11. A method of claim 10 wherein said anhydrous base comprises a metal alkoxide.

12. A method of claim 11 wherein said metal alkoxide comprises potassium t-butoxide.

13. A method for preferentially forming a (2S) 1,3-diamino-3-substituted-2-propanol chemical intermediate represented by the structural formula

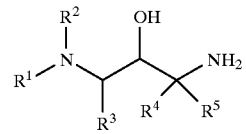

or salts thereof, wherein:
- $R^1$ is an amino protecting group;
- $R^2$ is selected from the group consisting of —H, C1–C18 alkyl, aryl, acetyl and tosyl;
- $R^3$ is a side-chain of an α-amino acid; and
- $R^4$ and $R^5$ are each independently selected from the group consisting of —H, alkyl, aryl, nitrile and alkoxycarbonyl, from an amino acid comprising the steps of:
   a) contacting said amino acid with an activating agent and an aprotic solvent under anhydrous conditions to form an activated amino acid;
   b) mixing a base with a nitromethane compound to form a nitromethane anion solution;
   c) contacting said activated amino acid with the nitromethane anion solution under anhydrous conditions to form a 3-amino-3-substituted-2-oxo-1-nitropropane;
   d) contacting said 3-amino-3-substituted-2-oxo-1-nitropropane with at least one carbonyl reducing agent that will reduce the carbonyl component of the 3-amino-3-substituted-2-oxo-1-nitropropane to preferentially form a 2S diastereomer, thereby preferentially forming a (2S) 1-nitro-3-amino-3-substituted-2-propanol compound; and
   e) contacting said (2S) 1-nitro-3-amino-3-substituted-2-propanol with a nitro reducing agent, thereby preferentially forming said (2S) 1,3-diamino-3-substituted-2-propanol chemical intermediate.

14. A method for preferentially producing a (2S) protease inhibitor synthetic intermediate represented by the formula

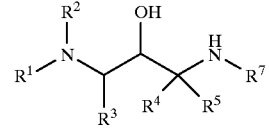

or salts thereof, wherein:
- $R^1$ is an amino protecting group;
- $R^2$ is selected from the group consisting of —H, C1–C18 alkyl, aryl, acetyl and tosyl;
- $R^3$ is a side-chain of an α-amino acid;
- $R^4$ and $R^5$ are each independently selected from the group consisting of —H, alkyl, aryl, nitrile and alkoxycarbonyl; and $R^7$ is selected from the group consisting of alkyl, hydroxyalkyl, alkoxyalkyl, cycloalkylalkyl, heterocycloalkyl, heterocyclo-alkylalkyl, aryl, heteroaralkyl, and aminoalkyl radicals, from a 3-amino-3-substituted-2-oxo-1-nitropropane, comprising the steps of:

a) mixing said 3-amino-3-substituted-2-oxo-1-nitropropane with at least one carbonyl reducing agent that will reduce the carbonyl component of said 3-amino-3-substituted-2-oxo-1-nitropropane to preferentially form a 2S diastereomer, thereby preferentially forming a (2S) 1-nitro-3-amino-3-substituted-2-propanol compound;

b) mixing said 1-nitro-3-amino-3-substituted-2-propanol with a nitro reducing agent, thereby preferentially forming a (2S) first chemical intermediate;

c) mixing said (2S) first chemical intermediate with $X^1$-$R^7$, wherein $X^1$ is a halogen radical, and with a base, thereby preferentially forming said (2S) protease inhibitor synthetic intermediate.

15. A diastereomerically-enriched composition predominantly comprising a compound represented by the formula

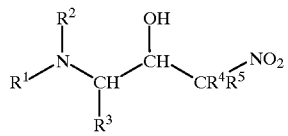

or salt thereof, wherein:

$R^1$ is an amino protecting group;

$R^2$ is selected from the group consisting of —H, C1–C18 alkyl, aryl, acetyl and tosyl;

$R^3$ is a side-chain of an α-amino acid; and $R^4$ and $R^5$ are each independently selected from the group consisting of —H, alkyl, aryl, nitrile and alkoxycarbonyl.

16. A compound of claim 15 which is a (2S) 3-amino-3-benzyl-1-nitro-2-propanol.

17. A composition predominantly comprising a 2S diastereomer of a compound represented by the formula

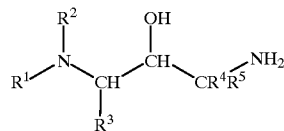

or salt thereof, wherein:

$R^1$ is an amino protecting group;

$R^2$ is selected from the group consisting of —H, C1–C18 alkyl, aryl, acetyl and tosyl;

$R^3$ is a side-chain of an α-amino acid; and $R^4$ and $R^5$ are each independently selected from the group consisting of —H, alkyl, aryl, nitrile and alkoxycarbonyl.

18. A compound of claim 15 which is a (2S) 1,3-diamino-3-benzyl-2-propanol.

19. A diastereomerically-enriched composition predominantly comprising a compound represented by the formula

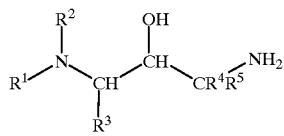

or salt thereof, wherein:

$R^1$ is an amino protecting group;

$R^2$ is selected from the group consisting of —H, C1–C18 alkyl, aryl, acetyl and tosyl;

$R^3$ is a side-chain of an α-amino acid; and $R^4$ and $R^5$ are each independently selected from the group consisting of —H, alkyl, aryl, nitrile and alkoxycarbonyl.

20. A compound of claim 19 which is a (2S) 1,3-diamino-3-benzyl-2-propanol.

21. A method of claim 1, wherein said reducing agent is a component in a composition that includes an optically pure compound.

22. A method for preferentially forming a (2S) 1,3-diamino-3-substituted-2-propanol chemical intermediate represented by the formula

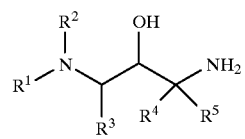

or salts thereof, wherein:

$R^1$ is an amino protecting group;

$R^2$ is selected from the group consisting of —H, C1–C18 alkyl, aryl, acetyl and tosyl;

$R^3$ is a side-chain of an α-amino acid; and $R^4$ and $R^5$ are each independently selected from the group consisting of —H, alkyl, aryl, nitrile and alkoxycarbonyl, comprising the step of contacting a 3-amino-3-substituted-2-oxo-1-nitropropane having the structural formula

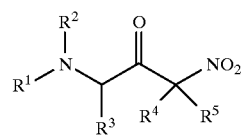

with at least one reducing agent that will reduce the carbonyl to preferentially form a 2S diastereomer and reduce the nitro group, thereby reducing said 3-amino-3-substituted-2-oxo-1-nitropropane to preferentially form said (2S) 1,3-diamino-3-substituted-2-propanol chemical intermediate.

23. A method of claim 2, wherein the reducing agent is lithium tri-tert-butoxyaluminohydride.

24. A method of claim 21, wherein the optically pure compound is (−) quinine.

* * * * *